United States Patent
Buckles et al.

[11] Patent Number: 6,027,500
[45] Date of Patent: Feb. 22, 2000

[54] CARDIAC ABLATION SYSTEM

[76] Inventors: David S. Buckles, 2670 Towle Dr., Palm Beach Gardens, Fla. 33410; Adrian F. Warner, 2010 Mainsail Cir., Jupiter, Fla. 33477

[21] Appl. No.: 09/072,881

[22] Filed: May 5, 1998

[51] Int. Cl.[7] .......................... A61B 17/39; A61B 5/0402
[52] U.S. Cl. ............................. 606/34; 606/41; 600/374; 600/509; 600/523
[58] Field of Search .................................. 600/374, 509, 600/523; 606/34, 40, 41; 607/99

[56] References Cited

U.S. PATENT DOCUMENTS

| | | | |
|---|---|---|---|
| 4,945,912 | 8/1990 | Langberg | 600/374 |
| 5,357,956 | 10/1994 | Nardella | 600/374 |
| 5,464,404 | 11/1995 | Abela et al. | 606/15 |
| 5,480,422 | 1/1996 | Ben-Haim | 607/122 |
| 5,573,533 | 11/1996 | Strul | 606/34 |
| 5,706,823 | 1/1998 | Wodlinger | 128/696 |
| 5,843,075 | 12/1998 | Taylor | 600/374 |

*Primary Examiner*—Lee Cohen
*Attorney, Agent, or Firm*—Fred Wiviott; Christian G. Cabou; Phyllis Y. Price

[57] ABSTRACT

An ablation system includes a catheter adapted to be inserted into the heart of a patient. The catheter has a distal end and a plurality of electrodes disposed adjacent the distal end. One of the electrodes being an ablation electrode. An ablation RF energy source connected to the ablation electrode, a patient interface is connected to at least some of the electrodes for acquiring intracardiac ECG signals and a stimulator is connected to the catheter for providing pacing signals thereto. A phase balanced all pass filter is connected between the catheter and the patient interface for suppressing the interference to the intracardiac ECG signals by the RF ablation energy signal.

18 Claims, 2 Drawing Sheets

CARDIAC ABLATION SYSTEM

BACKGROUND OF THE INVENTION

This invention relates to Cardiac ablation systems, and more particularly to a cardiac ablation system having a filter for filtering the ablation energy signal from intracardiac electrocardiogram wave forms.

One of the leading causes of death in the United States is cardiac arrhythmias, which are very rapid ineffectual contractions of the heart muscle. The most numerous cardiac arrhythmias are ventricular tachycardias (VT's) and supraventricular tachycardias (SVT's). SVT's originate in the left or right ventricle and are typically caused by arrhythmogenic sites associated with a prior myocardial infarction. SVT's originate in the atria and are typically caused by an accessory pathway. The presence of arrhythmogenic sites or accessory pathways located close to the inner surface of one of the heart chambers, can bypass or short circuit the normal electrical pathways potentially resulting in cardiac arrhythmia.

One method of treating tachycardias involves mapping the electrical activation sequence of the heart to locate the arrhythmogenic sites or accessory pathways and then to ablate the site by the application of a destructive energy source to the target tissue. Typical energy sources used for this purpose include direct current electrical energy, radio frequency electrical energy, laser energy and the like.

During the ablation process, the patient is monitored by acquiring ECG data from body surface electrocardiographs and intracardiac electrocardiograms while the patient's heart is paced by an external source. The amplitude of the electrogram wave forms derived from the electrodes placed in the heart are typically several orders of magnitude lower than the energy levels applied to the same catheter by the ablation generator. As a result, the application of radio frequency ablation energy interferes with at least some of the intracardiac electrocardiogram wave forms. Such interference produced by the application of ablation energy masks the underlying electrocardiogram wave form thereby negating the ability of the physician to monitor the electrocardiogram derived from the catheter electrodes through which ablation energy is applied.

SUMMARY OF THE INVENTION

It is an object of the invention to provide a cardiac ablation system in which intracardiac electrocardiograms can be monitored without interference from the ablation energy signal.

A further object of the invention is to provide a cardiac ablation system in which intracardiac electrocardiograms can be monitored without distortion during the application of the ablation energy signal.

It is another object of the invention to provide a cardiac ablation system having a filter for suppressing interference to intracardiac ECGs caused by the application of radio frequency ablation energy.

A further object of the invention is to provide a cardiac ablation system having a filter with linear phase response over the band width of interest which removes interference from electrocardiograms without wave form distortion.

Another object of the invention is to provide a cardiac ablation system having a filter which suppresses interference to intracardiac electrocardiogram wave forms caused by the application of radio frequency ablation energy to a patient without preventing the application of external pacing or other stimulation.

Yet another object of the invention is to provide a filter for use in a radio frequency cardiac ablation system which suppresses interference to intracardiac ECGs.

A still further object of the invention is to provide for use in a radio frequency cardiac ablation system a filter having linear phase response over the band width of interest which removes interference from ECGs without distortion. It is a further object of the invention to provide such a filter which does not prevent the application of an external pacing signal or other stimulation.

These and other objects and advantages of the invention will become more apparent from the detailed description of the invention taken with the accompanying drawings.

In general terms, the invention comprises an ablation system including a catheter adapted to be inserted into the heart of a patient, a plurality of electrodes disposed on the catheter and adjacent its distal end, one of the electrodes being an ablation electrode, an ablation RF energy source connected to the ablation electrode, a patient interface connected to at least some of the electrodes for acquiring intracardiac ECG signals and a phase balanced all pass filter connected between the catheter and the patient interface for removing the RF ablation signal from the intracardiac ECG signals.

DETAILED DESCRIPTION OF THE PREFERRED EMBODIMENT

Figure 1:
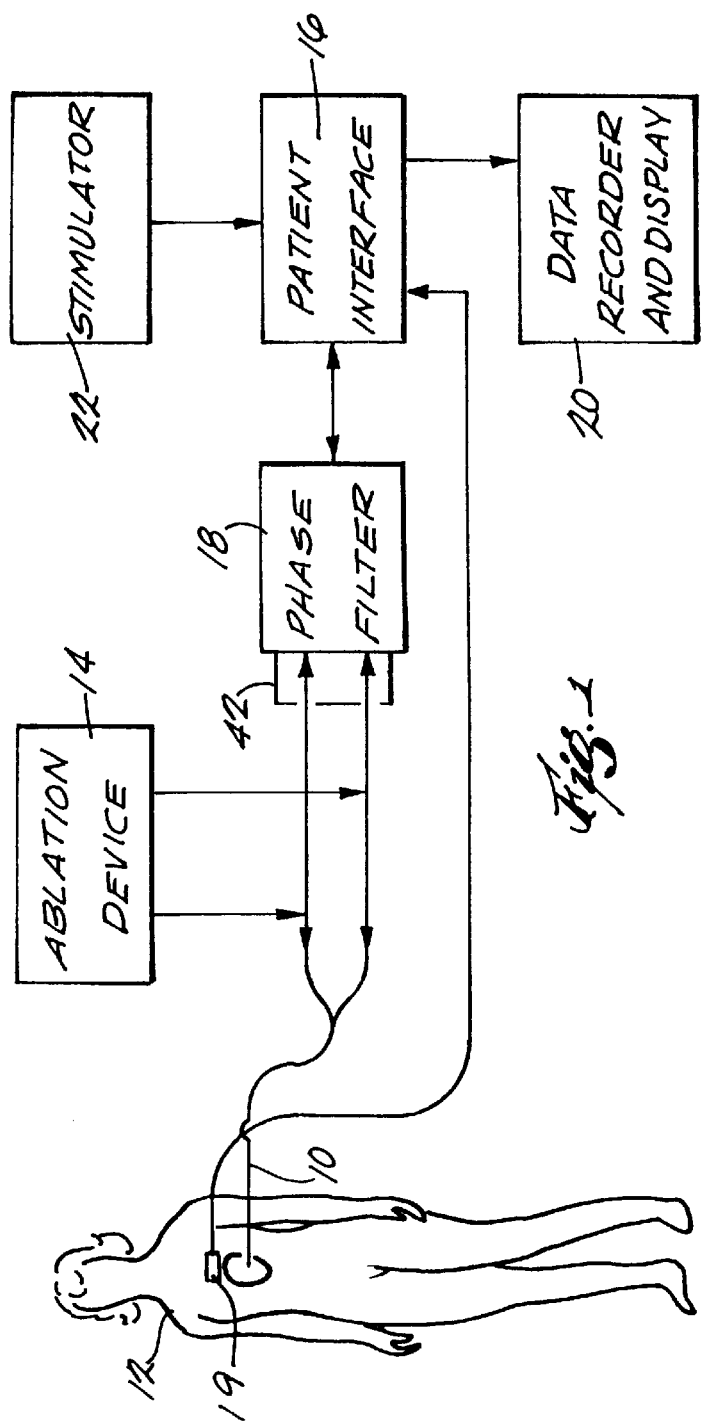
FIG. 1 shows a cardiac ablation system which incorporates the invention.

FIG. 1 shows an ablation system incorporating the present invention. The system includes a catheter 10 positioned in the heart of a patient 12 undergoing treatment. The catheter 10 is connected to an RF ablation energy source 14 for receiving RF energy. In typical ablation systems, about 30–50 watts of RF energy are supplied at a frequency of about 400–500 KHz. In order to monitor the patient during the ablation procedure, the catheter 10 is also connected to a patient interface 16 through a phase filter 18. The patient interface 16 receives the electrical signals from the catheter 10 and body surface electrodes 19 and generates the appropriate lead signals which are displayed on the data recorder and display 20. Also connected to the catheter 10 through the patient interface 16 is a stimulator 22 which provides pacing signals to the catheter 10. Pacing is provided to the patient from an external source 22 for purposes of diagnostics, such as arrhythmia induction and for life support if the patient's intrinsic heart rate becomes too low or experiences high grade conduction block.

The ablation device 14, the patient interface 16, the data recorder and display 20 and the stimulator 22 are all conventional and will not be discussed in detail for the sake of brevity. Typical components that may be employed include: an EPC-1000 by EP Technologies for the ablation device 14; an EP-2 by EP Medical for the stimulator 22; a Midas System by GE Marquette Medical Systems, Inc. for the patient interface 16 and a Blazer II Temperature Ablation Catheter by EP Technologies for the ablation catheter 10.

Those skilled in the art will appreciate that these are representative devices and that various other devices capable of performing the same or equivalent functions may also be employed.

Figure 2:
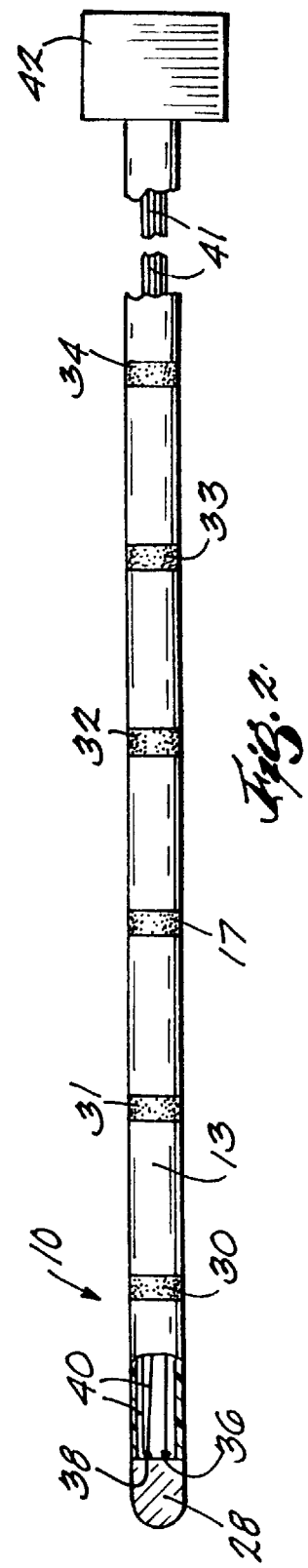
FIG. 2 shows a representative catheter usable with the system of FIG. 1.

The catheter 10 as shown in FIG. 2 typically comprises an elongate body 26 formed of an electrically insulating material, and having an ablation electrode 28 at its distal end. A plurality of ECG electrodes 30–34 are provided on the outer surface of body 26. While five ECG electrodes are illustrated, those skilled in the art will appreciate that the number may vary, depending on the number of ECG leads desired. The ablation electrode 28 may be connected by conductors 36 to the RF ablation energy source 14. In addition, a temperature sensor 38 is preferably connected by conductors 40 to the patient interface. The energy level provided by the ablation energy source should be sufficient to raise the target tissue to a temperature high enough to induce tissue necrosis. Typically, the temperature is above about 60° C. but generally does not exceed about 105° C. Temperature sensor 38 is provided for monitoring these temperatures.

While the ECG electrodes 30–34 may take any well known form, in the illustrated embodiment, these comprise rings in the outer surface of the body 26 and formed of any suitable conductive material. The ECG electrodes 30–34 are connected by conductors 41 to a socket 42 which in turn is coupled to the phase filter 18.

Those skilled in the art will appreciate that the target sites associated with tachycardia are identified by conventional intracardiac mapping procedures which are well known in the art. The surface electrodes 19, the intercardiac electrodes 30–34 and the stimulator 22 may be employed during the mapping procedure. The ablation catheter 10 is then percutaneously introduced, typically through the femoral vein or artery in the patient's groin. The distal end of the catheter containing the ablation electrode 28 is then manipulated in any suitable manner, such as by a guiding catheter, until the ablation electrode 28 contacts the desired region within interior of the heart chamber. Power at radio frequency is then applied to the target location from the ablation power generator 14. During this time, the patient's ECGs are monitored from the surface electrodes 19, the ablation electrode 28 and the electrodes 30–34 and pacing signals are applied to the patient's heart. However, it has been found that unless properly filtered, the signal generated when the ablation energy is being applied interfere with the intracardiac ECG's monitored by the electrodes 30–34. This interference is suppressed by the phase filter 18.

Figure 3:
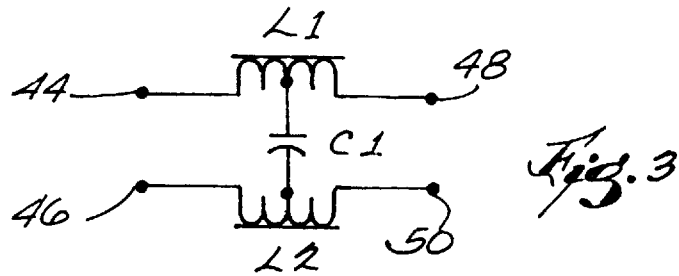
FIG. 3 shows the preferred embodiment of a filter usable with the system of FIG. 1.

The preferred embodiment of phase filter 18 is shown more particularly in FIG. 3 to comprise a phase-balanced or all pass analog electronic filter. The design is based on a first-order all pass transfer function that has a constant impedance over the entire frequency range of the filter. The filter includes center tapped inductors L1 and L2 connected in a bi-polar arrangement to a capacitor C1. The inductance of inductors L1 and L2 are equal and typically are in the range of 10–50 milliHenrys (mH) and the capacitance of capacitor C1 is in the range of 0.1–1.0 microFarada ($\mu$F). The catheter 10 is connected to terminals 44 and 46 and terminals 48 and 50 are connected to the patient interface 16. The bi-polar electrogram signal is transmitted from the catheter through the filter 18 to the patient interface 16.

Figure 4:
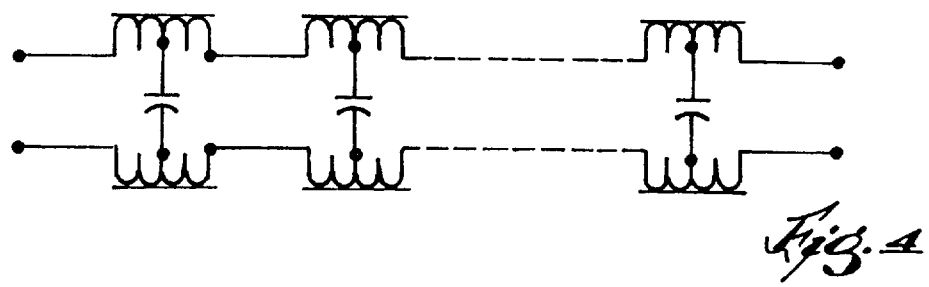
FIGS. 4–6 show alternate embodiments of filters usable with the system of FIG. 1.
Figure 5:
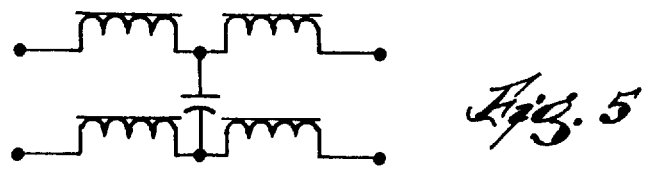
Figure 6:
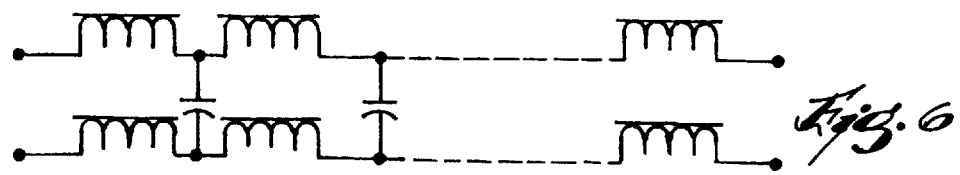

Alternate embodiments of the filter 18 are shown in FIGS. 4–6. The inductance and capacitance values for the embodiment of FIG. 4 are the same as for that of FIG. 3. FIGS. 5 and 6 show ganged or multiple versions of the embodiments of FIGS. 3 and 4, respectively, and while the impedance values vary they are similar to those of the embodiment of FIG. 3.

The amplitude of the electrogram wave forms derived from the electrodes placed in the heart are typically several orders of magnitude lower than the energy levels applied to the same catheter by the ablation generator. In the absence of the phase filter 18, the interference produced by the application of ablation energy would mask the underlying electrogram wave forms, thereby negating the ability of the physician to monitor the electrogram derived from the catheter electrodes to which ablation energy is applied. The phase filter 18 suppresses the interference to the intracardiac electrogram wave forms caused by the application of RF ablation energy provided to the patient via the catheter 10. In addition, bi-polar electrical continuity provided by the phase filter 18 allows for the conduction of external stimulus pulses from the stimulator 20 to the catheter 10. Also, the balanced bi-polar design eliminates any unbalance produced in a bipolar electrogram amplifier by standard monopolar or unbalanced analog filters. The bi-polar configuration provides linear phase response over the band width of interest eliminating phase related distortion of the electrocardiogram wave form commonly associated with analog filter implementations. The filter 18 also removes interference from the electrocardiogram without wave form distortion that is typically caused by analog electronic filter designs, and passes the electrogram to the patient interface essentially unchanged. This results in exceptional wave form fidelity while allowing the filter to be inserted into any recording system without hindering or altering the operation of the system or requiring any changes in operating procedures.

What is claimed is:

1. An ablation system comprising:
    a catheter adapted to be inserted into the heart of a patient and having a distal end,
    an ablation electrode disposed on said catheter and adjacent the distal end of the catheter,
    an ablation RF energy source connected to the ablation electrode and for producing an RF ablation signal,
    a patient interface connected to the ablation electrode for acquiring at least one intracardiac ECG signal, and
    a phase balanced all pass filter connected between the catheter and the patient interface for removing distortion caused by the RF ablation signal from the intracardiac ECG signals to be acquired by the patient interface.

2. The system set forth in claim 1 and including a stimulator connected to the catheter for providing a pacing signal thereto, said filter being connected between the catheter and the stimulator.

3. The system set forth in claim 2 wherein the catheter includes a plurality of ECG electrodes spaced apart from each other and from the distal end of the catheter, each of said electrodes being connected to the patient interface.

4. The system set forth in claim 3 wherein said filter is characterized by bi-polar electrical continuity and a linear phase response over the band width of the RF ablation energy signals.

5. The system set forth in claim 4 wherein said filter includes at least first and second inductors connected in a bipolar array and a capacitance connected therebetween.

6. The system set forth in claim 5 wherein said first and second inductors each comprise an inductor having a center tap and a capacitance connected therebetween.

7. The system set forth in claim 4 wherein the patient interface is operable to generate intracardiac ECG wave forms and display said wave forms.

8. The system set forth in claim 1 wherein the catheter includes a plurality of ECG electrodes spaced apart from each other and from the distal end of the catheter, each of said electrodes being connected to the patient interface.

9. The system set forth in claim 1 wherein said filter is characterized by bi-polar electrical continuity and a linear phase response over the band width of the RF ablation energy signals.

10. The system set forth in claim 9 wherein said filter includes at least first and second inductors connected in a bipolar array and a capacitance connected therebetween.

11. The system set forth in claim 10 wherein said first and second inductors each comprise an inductor having a center tap and a capacitance connected therebetween.

12. The system set forth in claim 1 wherein the patient interface is operable to generate intracardiac ECG wave forms and display said wave forms.

13. In an ablation system having a catheter adapted to be inserted into the heart of a patient, the catheter including a distal end, an ablation electrode positioned adjacent thereto, and at least one ECG electrode, an ablation RF energy source connected to the ablation electrode for delivering radio frequency ablation energy thereto and producing RF ablation signals, and a patient interface connected to at least one of the ECG electrodes, the improvement comprising:

a phase balanced all pass filter coupled between the catheter and the patient interface for removing the RF ablation signal from intracardiac ECG signals sensed by the at least one ECG electrode, the filter being characterized by bi-polar electrical continuity and a linear phase response over the band width of the RF ablation energy signals.

14. The system set forth in claim 13 wherein the filter comprises an LC all pass network having an input impedance which is constant over the band width of the RF ablation energy signals.

15. The system set forth in claim 14 wherein said filter includes at least first and second inductors connected in a bipolar array and a capacitance connected therebetween.

16. The system set forth in claim 15 wherein said first and second inductors each comprise an inductor having a center tap and a capacitance connected therebetween.

17. An ablation system comprising:

a catheter adapted to be inserted into the heart of a patient, the catheter having a distal end, an ablation electrode positioned adjacent the distal end, and an ECG electrode;

a stimulator connected to the catheter for providing a pacing signal thereto;

an ablation RF energy source connected to the ablation electrode and for providing an RF ablation energy signal;

a patient interface connected to the ablation electrode for acquiring at least one intracardiac ECG signal through the ECG electrode; and a phase balanced all pass filter connected between the catheter and the stimulator for removing the distortion caused by the RF ablation signal from intracardiac ECG signals to be acquired by the patient interface, said filter characterized by bi-polar electrical continuity and a linear phase response over the band width of the RF ablation energy signal and including at least first and second inductors connected in a bipolar array and a capacitance connected therebetween.

18. A system as set forth in claim 17 wherein said first and second inductors each comprise an inductor having a center tap and a capacitance connected therebetween.

* * * * *